United States Patent
Patricelli et al.

(10) Patent No.: US 7,174,302 B2
(45) Date of Patent: Feb. 6, 2007

(54) SYSTEM AND METHOD FOR PROCESSING FLEXIBLE SPENDING ACCOUNT TRANSACTIONS

(75) Inventors: Robert E. Patricelli, Simsbury, CT (US); Christopher M. Byrd, West Hartford, CT (US); Paul L. Chabot, West Granby, CT (US)

(73) Assignee: Evolution Benefits, Inc., New Haven, CT (US)

(*) Notice: Subject to any disclaimer, the term of this patent is extended or adjusted under 35 U.S.C. 154(b) by 1091 days.

(21) Appl. No.: 09/878,891

(22) Filed: Jun. 11, 2001

(65) Prior Publication Data

US 2002/0198831 A1 Dec. 26, 2002

(51) Int. Cl.
*G06Q 40/00* (2006.01)
*G06Q 50/00* (2006.01)

(52) U.S. Cl. ............................ 705/4; 705/39; 705/2
(58) Field of Classification Search ............... 705/4, 705/39
See application file for complete search history.

(56) References Cited

U.S. PATENT DOCUMENTS

| | | | | |
|---|---|---|---|---|
| 5,253,164 A | | 10/1993 | Holloway et al. ............... 705/2 |
| 5,384,449 A | * | 1/1995 | Peirce ............................ 235/380 |
| 5,550,734 A | | 8/1996 | Tarter et al. ................... 364/401 |
| 5,644,778 A | | 7/1997 | Burks et al. ..................... 705/2 |
| 5,689,100 A | * | 11/1997 | Carrithers et al. ............ 235/380 |
| 5,704,044 A | | 12/1997 | Tarter et al. ..................... 705/4 |
| 5,903,881 A | * | 5/1999 | Schrader et al. .............. 705/42 |
| 5,914,472 A | * | 6/1999 | Foladare et al. ............. 235/380 |
| 5,930,759 A | * | 7/1999 | Moore et al. .................... 705/2 |
| 5,991,750 A | | 11/1999 | Watson ........................... 705/44 |
| 6,012,035 A | | 1/2000 | Freeman, Jr. et al. .......... 705/2 |
| 6,029,144 A | | 2/2000 | Barrett et al. ................. 705/30 |
| 6,044,352 A | * | 3/2000 | Deavers .......................... 705/4 |
| 6,044,360 A | * | 3/2000 | Picciallo ........................ 705/21 |
| 6,067,522 A | | 5/2000 | Warady et al. .................. 705/2 |
| 6,108,641 A | | 8/2000 | Kenna et al. .................. 705/35 |
| 6,208,973 B1 | | 3/2001 | Boyer et al. ..................... 705/2 |
| 6,226,624 B1 | * | 5/2001 | Watson et al. ................. 705/44 |
| 6,253,998 B1 | * | 7/2001 | Ziarno .......................... 235/380 |
| 6,343,279 B1 | | 1/2002 | Bissonette et al. ............ 705/41 |
| 6,554,183 B1 | | 4/2003 | Sticha et al. ................. 235/379 |
| 6,738,749 B1 | * | 5/2004 | Chasko ........................... 705/17 |
| 2001/0027403 A1 | | 10/2001 | Peterson et al. ............... 705/4 |

(Continued)

OTHER PUBLICATIONS

Printout of Internet documents from the Fringe Benefits Management Company at (http://www.fbmc-benefits.com/).

(Continued)

*Primary Examiner*—Joseph Thomas
*Assistant Examiner*—Lena Najarian
(74) *Attorney, Agent, or Firm*—Thomas A. Corrado; Kilpatrick Stockton LLP

(57) ABSTRACT

A system and method are provided for processing flexible spending account transactions involving a plurality of pharmacies, a service provider, one or more pharmacy benefits managers ("PBMs"), and individuals having flexible spending accounts ("FSAs") and stored value cards for debiting their FSAs. The service provider maintains a PBM transaction database; receives from a pharmacy an authorization request at the time of purchase; queries the PBM transaction database for a matching transaction in response to the authorization request; and authorizes payment of the patient responsible balance to be automatically debited against the respective FSA at the time of purchase.

46 Claims, 5 Drawing Sheets

U.S. PATENT DOCUMENTS

| | | | |
|---|---|---|---|
| 2002/0002495 A1 | 1/2002 | Ullman et al. | 705/21 |
| 2002/0087444 A1 | 7/2002 | Dipiero et al. | 705/35 |
| 2002/0128879 A1 | 9/2002 | Spears | 705/4 |
| 2002/0138376 A1* | 9/2002 | Hinkle | 705/30 |
| 2002/0147678 A1 | 10/2002 | Drunsic | 705/39 |
| 2003/0009355 A1 | 1/2003 | Gupta | 705/2 |
| 2003/0061153 A1 | 3/2003 | Birdsong et al. | 705/39 |
| 2003/0074234 A1 | 4/2003 | Stasny | 705/4 |
| 2003/0130868 A1 | 7/2003 | Coelho | 705/2 |
| 2003/0149594 A1 | 8/2003 | Beazley et al. | 705/2 |
| 2003/0171953 A1 | 9/2003 | Narayanan et al. | 705/2 |
| 2004/0064386 A1 | 4/2004 | Goguen et al. | 705/34 |

OTHER PUBLICATIONS

Printout of Internet documents from the MedAdvantage Corporation at (http://www.medadvantage.com/).

Printout of Internet documents from Med-i-Bank at (http://www.medibank.com/).

Anonymous,"IRS branch chief fields cafeteria plan queries," Employee Benefit Plan Review, Vo. 53, No. 12, pp. 32-33, Jun. 1999.

Hamill, James R, "The design and operation of cafeteria plans," Tax Adviser, vol. 24, No. 10, pp. 657-664, Oct. 1993.

"Condor offers on-line verification systems," Chain Drug Review, vol. 13, No. 18, p. RX5(1), Jun. 17, 1991.

"drugstore.com, inc. and Evolution Benefits Make It Easier to Manage FSA-Eligible OTC Medication Expenses," Business Wire, p. 5224, Mar. 3, 2004.

"Eckerds' prescription for success is electronic claims", Computers in Healthcare, vol. 12, No. 6, pp. 51, Jun. 1991.

Carano, T., "IRS Guidance Provided on Debit Card Use", EBMC Report, Aug. 2003.

"Evolution Benefits Announces 2004 Technology Plans, Building on Industry Leading Capabilities, Announcement Also Corrects the Record on Substantiation Claims of Other Debit Card Companies", Internet Wire, Mar. 24, 2004.

Evolution Benefits Update On the Treasury Guidance on Use of Debit Cards with Flexible Spending Accounts (FSAs) and Health Reimbursement Arrangements (HRAs), Jun. 23, 2003.

Conn, J., "Instant Results: Blues plans in several states begin online claims adjudication", Modern Physician, vol. 5, Iss. 1, p. 6, Jan. 1, 2001.

O'Donnell, A., "IRS OKs Health Card Tech", Insurance & Technology, vol. 28, No. 13, p. 12, Dec. 2003.

Kuriyan, J.G., "New PHO concept eliminates middleman", Computers in Healthcare, vol. 13, No. 6, pp. 24(3), Jun. 1992.

"Payment Cards/Debit Cards . . . ",[online], Retrieved from the Internet: http://www.crbenefits.com/paymentcards.htm.

* cited by examiner

SYSTEM AND METHOD FOR PROCESSING FLEXIBLE SPENDING ACCOUNT TRANSACTIONS

BACKGROUND OF THE INVENTION

1. Field of the Invention

The subject invention relates to systems and methods for processing flexible spending account transactions, and more particularly, to an improved system and method for alleviating the need for the customer to provide an out-of-pocket payment at the time of sale and to later process a flexible spending account reimbursement for the patient responsible balance.

2. Background of the Related Art

A flexible spending account (hereinafter referred to as an "FSA") is a pre-tax account used to reimburse qualified medical expenses or patient responsible balances (hereinafter referred to as "PRBs") which would otherwise be paid directly by the plan participant. A FSA can be funded by an employer, employees or both. In the United States, the Internal Revenue Service (hereinafter "IRS") Code determines the types of expenses which are reimbursable. For example, some reimbursable expenses are co-payments and deductibles for health care expenses, vision expenses, ambulance expenses, oxygen equipment, wheelchairs, prescription drugs, and the like. FSAs are sponsored by employers and typically administered by a third party administrator (hereinafter referred to as a "TPA" or "FSA administrator"). Large employers may sponsor and administer FSAs independently.

Typically, the employee, i.e. account holder, designates a portion of his or her compensation into an FSA on a tax-free basis. The employee receives desired goods and services of which the employee's health insurance may pay for a portion or all of the cost. Generally, in the case of pharmacy transactions, the determination of the amount the employee's health insurance will pay is made by a pharmacy benefits manager (hereinafter referred to as a "PBM"). Often, the employee is required to pay at least a percentage or flat fee, e.g., the PRB. If the out-of-pocket employee payment is a qualified expense under the IRS Code, the employee completes and submits a claim form to the FSA administrator. Upon approval and processing, the proper amount is deducted from the employee's FSA and a reimbursement check is sent to the employee.

FSAs provide benefits to employers and employees by saving both tax dollars. Employers save in FICA taxes and employees save state, local, federal and FICA tax. Further, employers increase employee morale and retention, enhance their status in recruiting and provide flexibility to their employees. Employees garner the advantages of budgeting for qualified expenses and directing how their FSA money is spent.

Techniques for automating the processing of financial transactions are ubiquitous. One example is illustrated in U.S. Pat. No. 6,208,973 to Boyer et al. which shows a point of service third party adjudicated payment system. The system is accessed by patients, i.e. cardholders, who utilize a plurality of providers, such as doctors, hospitals and pharmacies. Each provider has a point of service terminal associated therewith. The point of service terminals connect, via the Internet, with an Internet Merchant Bank, which maintains accounts for the cardholders. Third party payors employ the system to reduce administrative costs. The third party payor is typically an HMO who contracts with the cardholder's employer. An adjudication engine is directly connected to the Internet Merchant Bank. The adjudication engine pays the providers, bills the third party payor and bills the cardholder by utilizing a processor which interacts with a multitude of databases. In use, the provider sends information to the adjudication engine via the point of service terminal. The adjudication engine determines the obligations of the third party payor and the cardholder, and the Internet Merchant Bank pays the obligations and updates the balances accordingly in a real-time manner.

U.S. Pat. No. 5,644,778 to Burks et al. illustrates a medical transaction system which permits a plurality of healthcare provider computer stations to communicate with a plurality of payors and financial institutions. The medical transaction system facilitates processing medical claims. A financial transactor generates electronic finds transfers in order to credit and debit accounts. The financial transactor may also generate credit authorization to allow determining if a credit line is available to pay a remaining amount of a claim. If a credit line is available, the financial transactor generates a message to allow payment of the remainder. Additional references, such as U.S. Pat. No. 5,991,750 to Watson, show clearinghouse processing facilities for processing claims. Further examples are U.S. Pat. No. 6,067,522 to Warady et al. and U.S. Pat. No. 5,704,044 to Tarter et al. which show healthcare account and billing processing systems and methods. Each of the patents above are incorporated herein by reference to the extent they do not conflict with the subject disclosure.

In other prior art systems, PBMs retain credit or debit card numbers for customers on file in order to direct bill mail order pharmacy transactions. Accordingly, when adjudicating claims for mail order pharmacies, the PBMs may direct bill the customers' credit or debit cards for the PRB.

Various other systems have been developed that provide consumers with stored value cards that are intended to allow consumers to electronically debit their FSAs for the PRB, rather than pay the PRB at the time of a transaction and later seek reimbursement therefor. One of the difficulties encountered in these types of systems is that the information directly available in connection with stored value card transactions (such as the merchant category code and purchase amount) is insufficient to substantiate the expense under the IRS Code. For example, in a typical pharmacy there are thousands of products that may be purchased that are not reimbursable under the IRS Code. Thus, if a purchaser simultaneously purchases both reimbursable and non-reimbursable items, the information typically provided by a stored value card transaction (e.g., merchant category code and purchase amount) is insufficient to substantiate the expense.

Accordingly, there is a need for an improved system and method for processing FSA transactions which assures that only allowed expenses are reimbursed, alleviates onerous paperwork, enables customers to pay the PRB from their FSA without providing money at the time of purchase, and/or maintains accurate records for review by the employee, employer and FSA administrator.

SUMMARY OF THE INVENTION

The present invention is directed to a system and method for processing flexible spending account transactions. A service provider maintains the system which comprises at least one computer memory for storing a program, and a transaction database of transactions adjudicated by one or more payors, such as a PBM. Preferably, the service provider issues to participating customers, either directly or indirectly through, for example, an employer, TPA or FSA administrator, stored-value cards associated with the customers' respective FSAs. At the time of purchasing goods or services from a goods or service provider, such as a pharmacy, the goods or service provider electronically transmits to a respective payor, such as a PBM, the claim information, including, for example, a customer or participant identifier, provider identifier, and purchase information. The payor adjudicates the claim, i.e., determines whether the participant has insurance coverage, the amount to be paid by the insurer, and the PRB. The payor then transmits back to the goods or service provider the PRB. Upon completing the transaction with the goods or service provider, the payor transmits the transaction data to the service provider, and the service provider stores the transaction data in the payor transaction database. The transaction data preferably includes a participant or customer identifier, date and time of the transaction, and the PRB. Then, data relating to the customer is captured. Preferably, the customer is a card holder and the customer-related information is captured by, for example, swiping his or her FSA card through a card reader device located at the goods or service provider to, in turn, transmit to the service provider a request to authorize payment of the PRB from the customer's FSA. The request to authorize payment may include, for example, a card holder identifier, an identifier of the provider, merchant category code, the time of the transaction, and the PRB requested.

In response to the request to authorize payment, a microprocessor unit of the system queries the payor transaction database for a payor transaction matching the customer's request to authorize payment. Preferably, the transaction database is queried to find the matching transaction based on the customer identifier corresponding to the respective card holder identifier, such as, without limitation, a social security number or individual participant number assigned by a respective PBM or FSA administrator. If a matching transaction is found and if there are sufficient funds in the customer's FSA, the microprocessor then transmits to the goods and service provider authorization for payment of the requested PRB from the customer's FSA and the customer otherwise need not pay anything to the provider at the time of the transaction. If, on the other hand, a matching transaction is not found, or if the customer has insufficient funds in his or her FSA, then the processor rejects the request for authorization.

One advantage of the system and method of the present invention is that the payors, such as PBMs, adjudicate only IRS allowed expenses. As a result, the payor transaction database allows the service provider to rapidly and reliably substantiate whether the expenses associated with the requests for authorization are IRS allowed expenses simply by confirming that each customer request transaction matches a corresponding transaction in the payor transaction database. Another advantage of the system and method of the present invention is that they enable card holders to debit the PRBs involved in pharmacy or other provider transactions directly against their FSAs through the stored-value cards, and thereby avoid the inconvenience otherwise associated with providing the PRBs at the goods or service providers and later seeking reimbursement of the PRBs from their FSAs. Yet another advantage of the present invention is that the payor transaction database may retain sufficient information to enable the service provider to later prove the specific prescription drug or other item that was the subject of the transaction was properly reimbursable, as may be required by the IRS, for example.

These and other unique features and advantages of the system and method of the invention will become more readily apparent from the following description, the accompanying drawings and the appended claims.

BRIEF DESCRIPTION OF THE DRAWINGS

So that those having ordinary skill in the art to which the disclosed system and method appertains will more readily understand how to make and use the same, reference may be had to the drawings wherein.

DETAILED DESCRIPTION OF THE PREFERRED EMBODIMENTS

The present invention overcomes many of the prior art problems associated with administering FSAs. The advantages, and other features of the systems and methods disclosed herein, will become more readily apparent to those having ordinary skill in the art from the following detailed description of the preferred embodiments taken in conjunction with the drawings which set forth a representative embodiment of the present invention.

Figure 1:
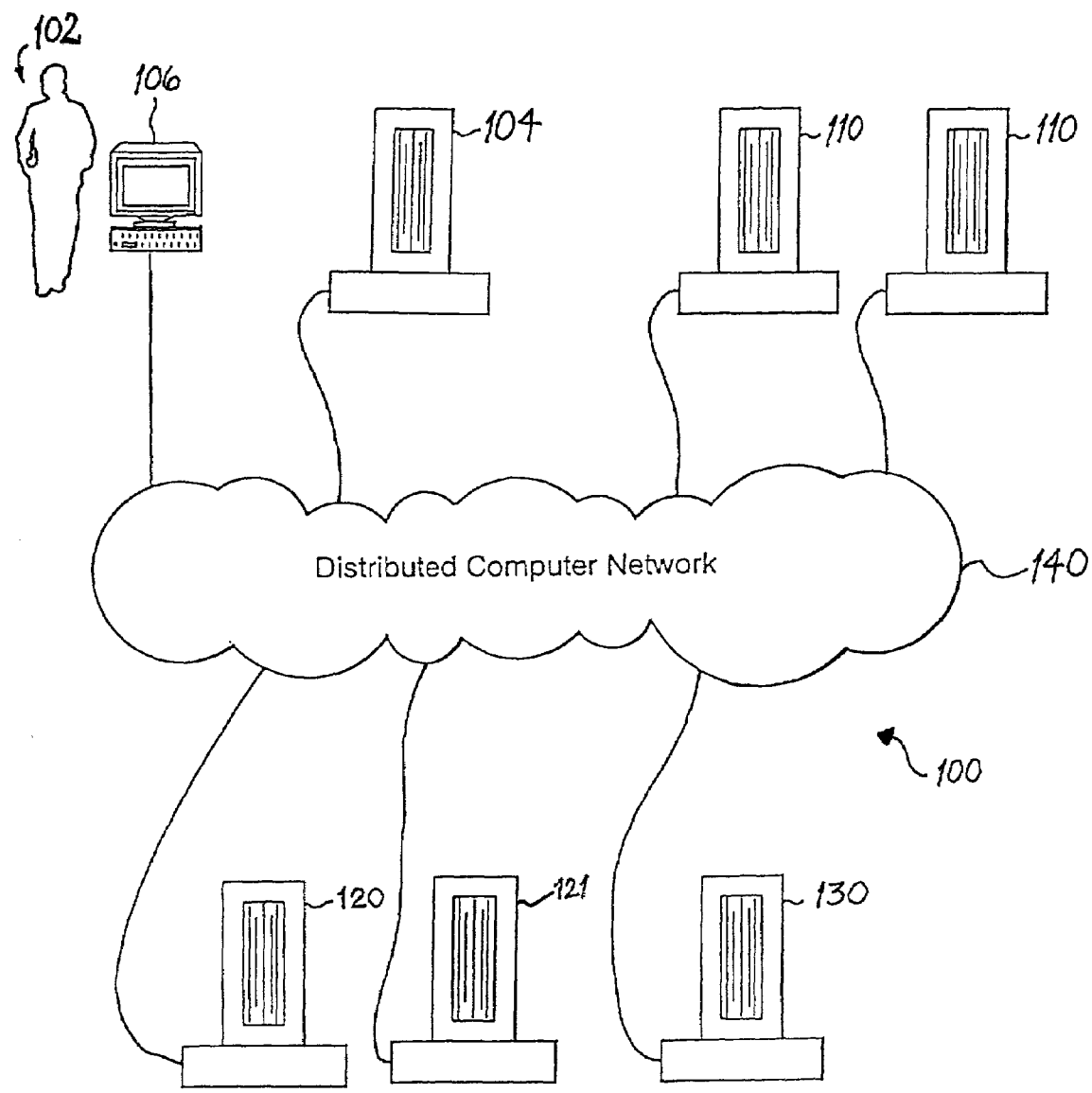
FIG. 1 is a schematic illustration of a system embodying the present invention for processing FSA transactions.

Referring to FIG. 1, a schematic illustration of a system, designated generally by the reference numeral 100, provides access to a FSA for an employee 102 of a sponsoring employer 104. The system 100 includes a plurality of goods and/or service providers, such as pharmacies 110, a service provider 120 for maintaining the system and processing the FSA transactions in accordance with the invention and described further below, one or more TPAs 121, and one or more payors, such as PBMs 130. If desired, the employee 102 may have a personal computer 106 associated therewith. Although only one employee 102, one personal computer 106 and one employer 104 are illustrated, it is understood that a plurality of employees and employers may simultaneously reap the advantages and benefits of the subject disclosure. Similarly, only two pharmacies 110, one TPA 121 and one PBM 130 are shown for simplicity; however, numerous pharmacies and/or other goods and service providers 110, TPAs 121 and PBMs and/or other payors 130 may simultaneously participate in the subject disclosure.

The term "payor" is used herein to mean any entity that adjudicates claims for payment or reimbursement of qualified medical expenses under the IRS code and is in a position to transmit data relating to such adjudicated transactions to a service provider 120 in accordance with the present invention. As indicated above, claim adjudication typically involves determining whether the participant has insurance coverage, the amount to be paid by the respective insurer, and balance of the transaction amount owed by the participant. As also indicated above, the balance of the transaction amount owed by the participant is referred to herein as the "patient responsible balance" or "PRB". The term "patient responsible balance" and acronym "PRB" as used herein do not require that the participant actually be a "patient" in the ordinary sense of the word; rather, this term and acronym simply refer to the balance of the transaction amount owed by the participant who frequently is, but need not be, a patient. The term "pharmacy benefits manager" and acronym "PBM" are used herein to refer to a specific type of "payor", and therefore contemplate, without limitation, any entity that adjudicates pharmacy transactions and provides data to the service provider 120 to substantiate whether the expenses involved in a pharmacy transaction are allowed for reimbursement under the IRS Code. In the preferred embodiment, the PBMs 130 adjudicate each pharmacy transaction, i.e., the PBMs determine whether a card holder has insurance coverage, the amount of the transaction to be paid by the respective insurer, and the PRB.

As may be recognized by those skilled in the pertinent art based on the teachings herein, although the goods and/or service providers in the illustrated embodiment are pharmacies 110, the system and method of the present invention contemplate any of numerous different types of goods and/or service providers in lieu of, or in addition to the pharmacies.

For example, the goods and/or service providers 110 may include, without limitation, physicians, hospitals, ambulatory surgery centers, vision care specialists, dentists, and the like. One exemplary method of obtaining the necessary data from non-pharmacy transactions is to receive the necessary data from the relevant health insurer or TPA. Another alternative method would be for the service provider 120 to receive the necessary data to populate the databases from one or more central clearing houses which the transactions are routed through. Further still, although the payors in the illustrated embodiment are PBMs 130, the system and method of the present invention contemplate in lieu of, or in addition to the PBMs, any of numerous different types of entities that are currently, or later become known for performing the function of adjudicating claims for payment or reimbursement of qualified medical expenses under the IRS code.

Each of the entities within the system 100 communicates over a distributed computing network 140 with commonly known communication links. Each of the entities within the system 100 include internal architectures, interfaces, and communication devices (e.g., modems) to enable processing, communication and security. For the purpose of simplicity and clarity, a detailed description of the same is omitted because they are well known in the art. In a currently preferred embodiment, the entities communicate via direct modem connection, satellite, and the like. In another embodiment, the distributed computing network 140 is at least partly the Internet.

In a preferred embodiment, the employer 104, the service provider 120, the TPA 121 and the PBM 130 each provide a server in communication with the distributed computing network 140. The servers may be a standalone computer or multiple networked computers that are located at one physical location. In the case of networked computers, they communicate according to well established network protocols. Alternatively, each server may include multiple computers that are networked together across multiple physical locations in a known manner and that communicate with each other via well-known communication techniques. In this way, as is well known in the art, memory and processing may be distributed among the computers that may make up the server in order to enhance performance and stability.

Typically, a server includes memory and at least one processor in communication therewith. Memory typically includes one or more machine readable media. Such media include, as is well known in the art, magnetic and/or optical media, such as a hard disk, optical disk, floppy disk, tape, random access memory, read only memory, and/or a combination thereof. The memory (or portions thereof) may reside on a single computer, or may be distributed in a known manner among multiple computers that may be included in the server. The pharmacies or other goods or service providers 110 provide a plurality of transaction devices to conduct sales such as, without limitation, a cash register, magnetic card reader and personal computer, and each transaction device is capable of being in communication with a local server or network. Such transaction devices are also configured to send and receive information with the service provider 120 and one or more PBMs or other payors 130. These transaction devices and communication protocols are well known to those skilled in the art and, therefore, are not further described herein.

Figure 2:
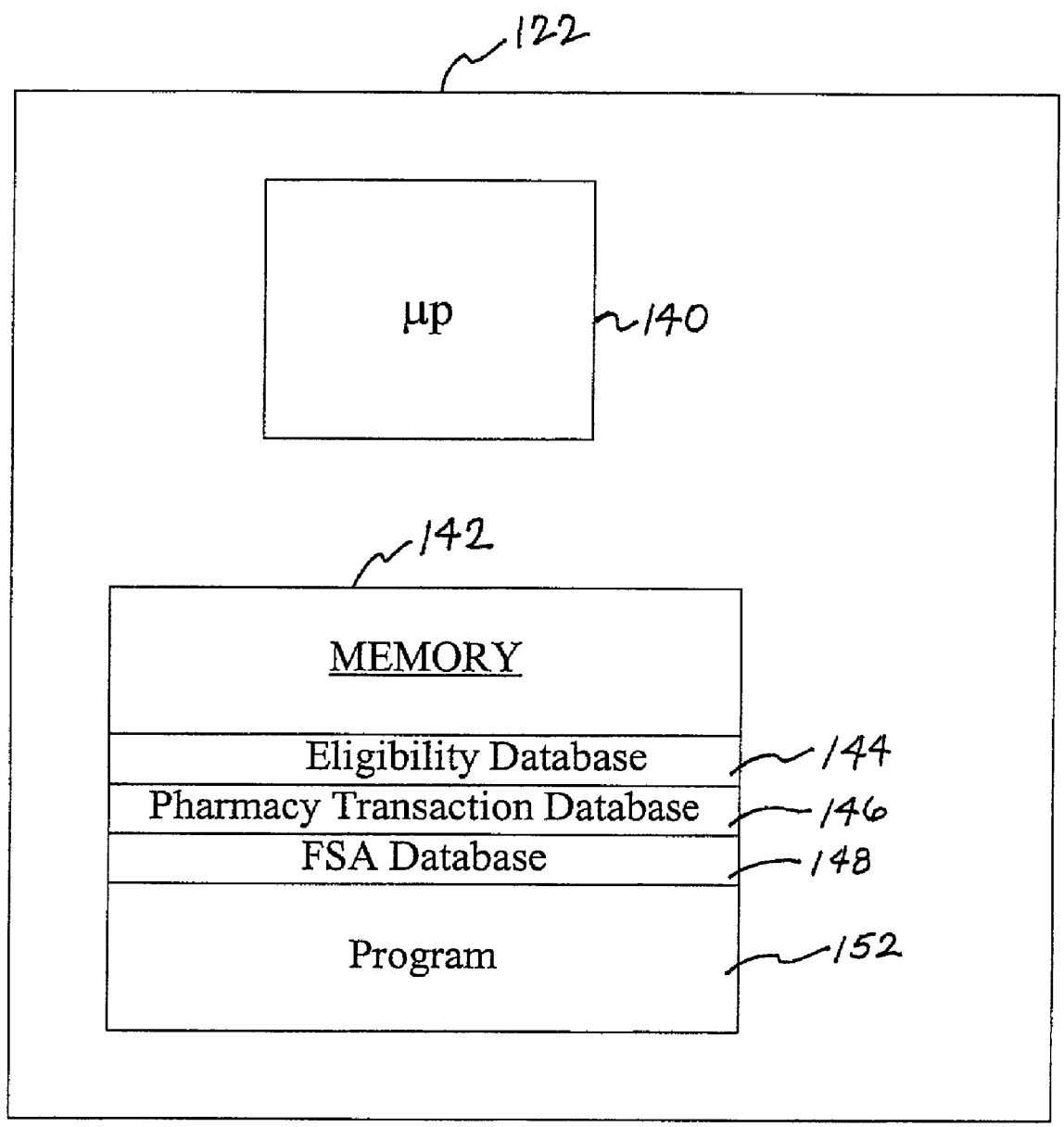
FIG. 2 is a diagrammatic representation of a server of the service provider of FIG. 1.

Referring to FIG. 2, the server 122 of the service provider 120 stores data relating to employees who have FSAs in the form of a computerized list, e.g., a database. The server 122 will provide FSA account history to the employee 102, employer 104, and TPA 121. It is envisioned that the data relating to the employees that is stored by the server 122 includes data that identifies each employee, i.e. a customer or participant identifier. The terms "customer identifier" and "participant identifier" are used herein interchangeably, and preferably are defined by a unique number, alphanumeric or other designation associated with each employee, such as a social security number, a number assigned by the employer 104 and the like. Additionally, the server 122 stores data relating to transactions which have occurred at the pharmacies and/or other goods or service providers 110 in a payor transaction database. In one embodiment, the data relating to such transactions includes a participant identifier, time of the transaction, and the PRB.

The server 122 has a processor 140 and memory 142. The memory 142 includes an eligibility database 144, a payor transaction database 146, and a FSA database 148. A typical record in the eligibility database 144 includes fields for the record type, social security number of the employee, the employee's name and any qualified spouse and dependants. The record type may be set to add, terminate or file trailer. A typical record in the payor transaction database 146 includes a participant identifier (e.g., a social security number), the PRB, and date and time of transaction. A typical record in the FSA database 148 includes the employee's name, social security number and FSA balance. Preferably, the databases are used in a relational arrangement, as is known in the art, so that they relate to one another by way of fields that store common data.

Referring once again to FIG. 2, memory 142 also includes a program 152 that executes the functions of the server 122 in accordance with the subject disclosure. The program 152 comprises computer instructions and/or data, executable or otherwise which are performed by the processor 140 of the server 122. In one embodiment, the program 152 allows the server 122 to receive, store and transmit data to the pharmacies or other goods or service providers 110, computer 106 of the employee 102, employer 104, the TPA 121 and PBMs or other payors 130. In a preferred embodiment, the server 122 receives, stores and transmits data over the distributed computer network 140.

Prior to an employee 102 taking advantage of the disclosed system, an employer 104 contracts with a TPA 121. In turn, the TPA 121 contracts with the service provider 120 in order to offer the system and method of the invention as a benefit to their employees 102. If the employer 104 is administering the FSA program independently, the employer 104 contracts directly with the service provider 120. Upon engagement, the employer 104 or TPA 121, as the case may be, provides enrollment data relating to the participating employees 102 to the server 122 of service provider 120. The processor 140 of the server 122 populates the eligibility database 144 and FSA database 148. However, the dynamic environment of the workplace requires adding and removing employees 102 to insure that the eligibility database 144 is accurate. An out-of-date eligibility database 144 can result in improper reimbursements.

Figure 3:
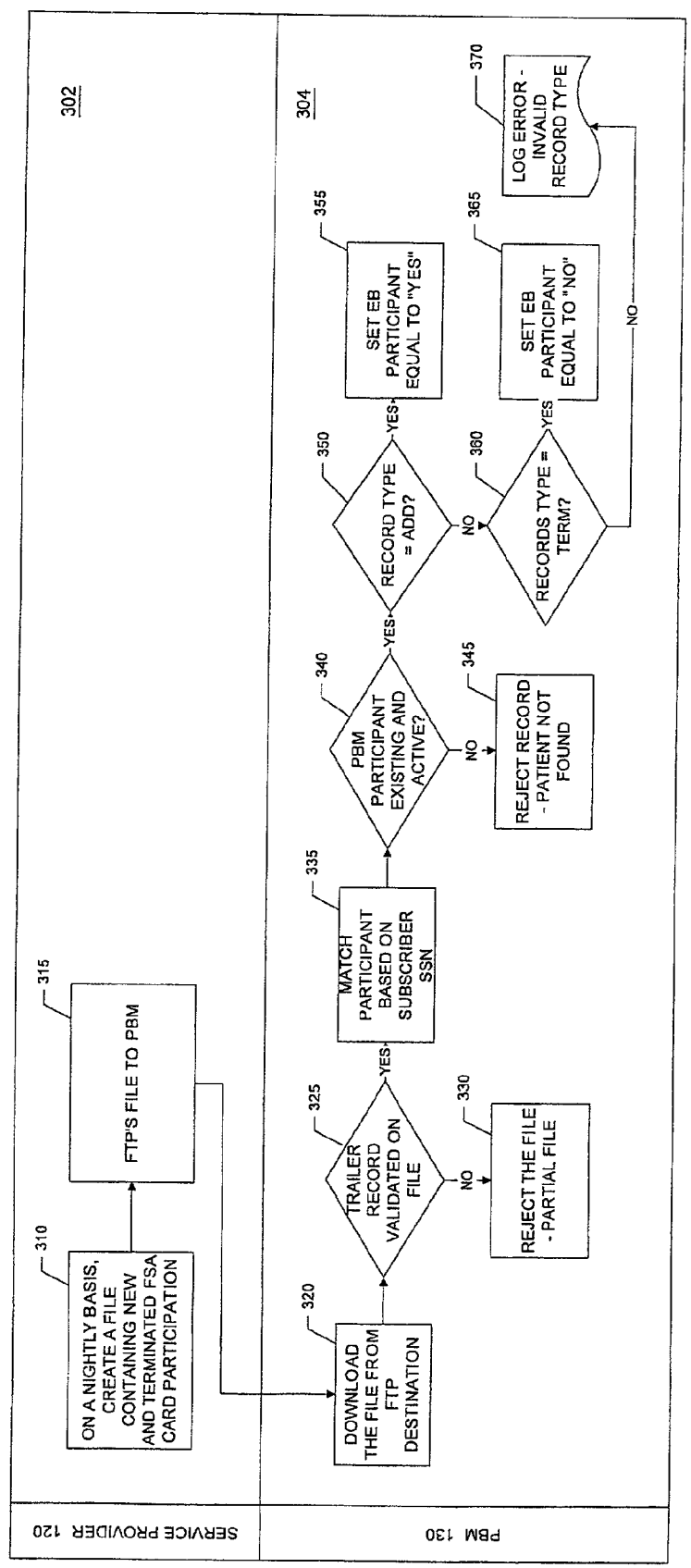
FIG. 3 depicts a process for maintaining an eligibility database in accordance with the present invention.

Referring now to FIG. 3, a presently preferred method for maintaining the accuracy of the eligibility database 144 is shown. The actions performed by the service provider 120 and the PBMs 130 are located in the service provider row 302 and PBM row 304, respectively. At step 310, the service provider 120 receives from the employer 104 or the TPA 121 data relating to eligibility of employees 102. Preferably, the eligibility data includes a participant identifier and a record type. In one embodiment, the participant identifier is the customer's social security number. In another embodiment, the participant identifier is a plan participant number assigned by the employer 104, the TPA 121, or the PBM 130. The record type indicates whether to add or terminate the employee 102 associated with the social security number.

Depending upon the urgency, the eligibility data may be transferred to the service provider 120 immediately, hourly, daily, monthly or the like. It is currently envisioned that the eligibility data is received daily. Accordingly, on a nightly basis, the service provider 120 populates the eligibility database 144.

At step 315, the service provider 120 creates a file containing a trailer record and the eligibility data, and provides the file to the PBM 130. In one embodiment, the file transfer is by well known communication protocols across the Internet. For example, the file may be located at an Uniform Resource Locator (hereinafter "URL") from which it can be downloaded. The URL is an address that defines the route to the file on the Web or any other Internet facility. The PBM 130 types in the URL to access the file as a Web page. In another embodiment, the service provider 120 transfers the file directly to a specific directory on the server of the PBM 130.

At step 320, the PBM 130 downloads the file containing the eligibility data. The PBM 130 requires the eligibility data in order to prevent transmitting to the service provider 120 transaction data in connection with ineligible employees. At step 325, the PBM 130 evaluates whether or not the trailer record associated with the eligibility data is verified because unverified eligibility data should not be used. If the trailer record is not verified, the processing of the respective eligibility data terminates at step 330. If the trailer record is verified, the processing continues at step 335.

At step 335, the PBM 130 extracts each record within the eligibility data and queries the PBM eligibility database stored on the PBM server for a match based upon a participant identifier, such as social security number or participant number. At step 340, the PBM 130 determines if the record corresponds to an existing and active employee 102 within the PBM eligibility database. If a matching record is not found, i.e. the employee 102 is not currently in the PBM eligibility database maintained by the PBM 130, the processing for that record terminates at step 345 where the record is rejected. Further, if a matching record is found but the status is not "active", the processing also terminates at step 345. Alternatively, if the record is found and the status is "active", the processing continues to step 350.

At step 350, the PBM 130 determines the appropriate action based upon the record type. If the record type is "active", the processing continues to step 355. At step 355, an indicator flag associated with the employee 102 in the PBM eligibility database is set to "yes" to indicate that the employee 102 has a FSA and is covered by the PBM 130. Additionally, like records for all eligible dependents of the employee 102 are established within the PBM eligibility database. If the record type is not "active", the processing continues to step 360.

At step 360, the PBM 130 continues to determine the appropriate action based upon the record type. If the record type is "terminate", the processing continues to step 365. At step 365, the indicator flag of the eligibility record of the employee 102 and all eligible dependents in the PBM eligibility database is set to "no". If the record type is not "terminate", the processing continues to step 370. At step 370, the server of the PBM generates an error message, associates the message with the record, and stores the error message in an error database.

In another preferred embodiment, the PBM 130 receives the eligibility data from the service provider 120. Rather than flagging records in its PBM eligibility database, the PBM 130 stores the eligibility data in a separate database. When the PBM 130 receives a claim from a pharmacy 110, the PBM 130 queries the separate database to determine if the claim is associated with an eligible employee 102.

Figure 4A:
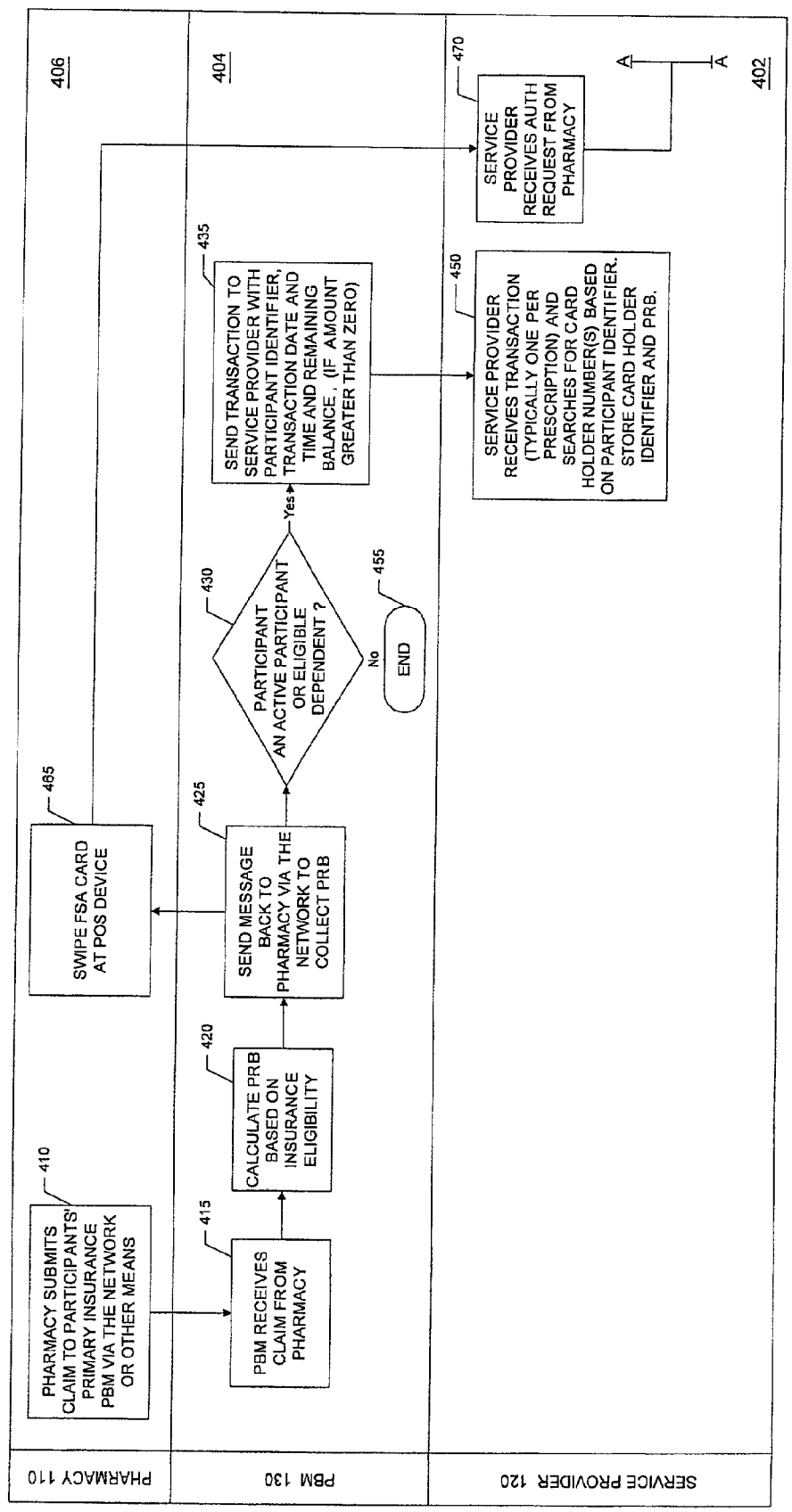
FIG. 4A depicts a first portion of a process for processing FSA transactions in accordance with the present invention.

Referring now to FIG. 4A, prior to an employee 102 utilizing the benefits of the subject disclosure, the service provider 120 issues a stored-value card (also referred to herein as a "FSA" card) to the employee 102 based upon enrollment in a program sponsored by the employer 104. It is envisioned that although employee 102 is used throughout the specification to refer to an individual with a FSA and associated FSA card, it will be understood that qualified dependents, spouses and other eligible non-employees would fully participate in the advantages and benefits of the system and method disclosed herein in a similar manner to that of an employee 102. Preferably, the eligible non-employees would receive their own respective FSA cards associated with the employee's FSA.

Still referring to FIG. 4A, the actions performed by the service provider 120, the PBM 130 and the pharmacy 110 are located in the service provider row 402, PBM row 404 and the pharmacy row 406, respectively. For the purposes of clarity and simplicity, the reward and notification of a single employee 102 is described with respect to a single transaction at a pharmacy 110. Of course, it is contemplated that the subject disclosure will be used to compensate a multitude of employees 102 associated with a plurality of employers 104 who utilize the services offered by the service provider 120 in connection with transactions at any of numerous different types of goods and/or service providers, such as pharmacies, that may be associated with any of numerous different types of payors, such as PBMs 130. To accommodate such processing of multiple employees 102, multiple providers 110 and payors 130, the process may be modified accordingly as would be known to those of ordinary skill in the pertinent art based on the teachings herein.

At step 410, the employee 102 begins a purchase at a pharmacy 110. For example, the employee 102 may request the pharmacy 110 to fill a prescription. As is customary, the employee 102 provides insurance information to the pharmacy 110. The pharmacy 110 submits a claim to the employee's PBM 130. Each such electronic data interchange preferably occurs over a network in a secure environment as is known to those skilled in the art and, therefore, is not further described herein.

At step 415, the PBM 130 receives the claim from the pharmacy 110. At step 420, the PBM 130 adjudicates the claim, i.e. calculates the payments to be made by the employee's insurance company and the PRB. At step 425, the PBM 130 transmits a message to the pharmacy 110 indicating the PRB. From step 425, the processing of the transaction continues without interruption to steps 430 and 465.

At step 430, the PBM 130 determines if the employee 102 is an "active" status. To determine employee status, the PBM 130 preferably queries the PBM eligibility database. As noted above, the PBM 130 maintains a PBM eligibility database based upon the eligibility data received from the service provider 120. If the employee status is "active", processing continues to step 435. If the employee status is not "active", the processing proceeds to step 455 in which case the PBM 130 will not send the transaction data to the service provider 120. In that case, the employee 102 will not be able to use his or her FSA card for that transaction and would need to pay the PRB by traditional methods.

At step 435, provided the PRB is greater than zero, the PBM 130 transmits data relating to the transaction to the service provider 120 and the processing continues to step 450. The data relating to the transaction preferably includes the participant identifier, such as an employee social security number, the time and date of the transaction and the PRB. If the PRB is less than or equal to zero, the PBM 130 takes no action and the processing terminates.

At step 450, the service provider 120 receives the data relating to the transaction and the microprocessor 140 populates the databases in memory 142. For example, the payor transaction database 146 is populated with a record for each payor transaction. Additionally, the service provider 120 retrieves the card holder identifier associated with the FSA card of the employee 102 based on the participant identifier. Preferably, the retrieval is based upon a search using the employee's social security number or other participant identifier. Thus, the databases contain the PRB, the card holder identifier, and the participant identifier, such as social security number, or the participant number assigned by the service provider 120 or TPA 121. The card holder identifier is preferably a sixteen digit number or other unique numeric or alphanumeric designation appearing or otherwise located on the respective FSA card. Preferably, a magnetic strip on the FSA card stores the unique number or designation, and in a currently preferred embodiment, the card holder identifier is a typical sixteen digit number as customarily used by issuers of credit, debit and stored value cards. As may be recognized by those skilled in the pertinent art based on the teachings herein, a participant identifier might be matched to more than one card holder identifier. For example, a husband and wife may each have his and her own individual FSA and insurance coverage. Under such circumstances, the PRBs for either individual are allowed to be reimbursed from either FSA regardless of which insurance covers the claim because the transaction is associated with both card holder identifiers.

At step 465, when the employee 102 receives his or her prescription, the pharmacy 110 requests payment of the PRB. In order to enable payment of the PRB directly from the FSA at that time and alleviate the need, subsequently, to file a reimbursement request to the FSA administrator, the employee 102 provides his or her FSA card to the pharmacy 110. The pharmacy 110 preferably swipes the FSA card through a point of sale device (hereinafter referred to as a "POS" device), such as a magnetic card reader, similar to the method employed with a traditional credit or debit card. However, as may be recognized by those of ordinary skill in the pertinent art based on the teachings herein, the FSA card information may be collected and transmitted by the pharmacy or other goods or service provider in any of numerous other ways that are currently, or later become known for performing this function. For example, the FSA card information may be input by keyboard or other input device for collection and transmission to the service provider as disclosed herein.

Still referring to step 465, the pharmacy 110 submits an authorization request to the service provider 120 as a result of reading the FSA card or otherwise inputting the FSA information. In a presently preferred embodiment, the authorization request includes the card holder identifier, the payment amount requested, a date and time of the transaction, a merchant identifier and a merchant category code ("MCC"). However, as may be recognized by those skilled in the pertinent art based on the teachings herein, the authorization request may include any of numerous other types of information in addition to, or in lieu of such information, in order to perform the function of the authorization request as disclosed herein. At step 470, the service provider 120 receives the authorization request from the pharmacy 110 and processing continues to step 475.

Figure 4B:
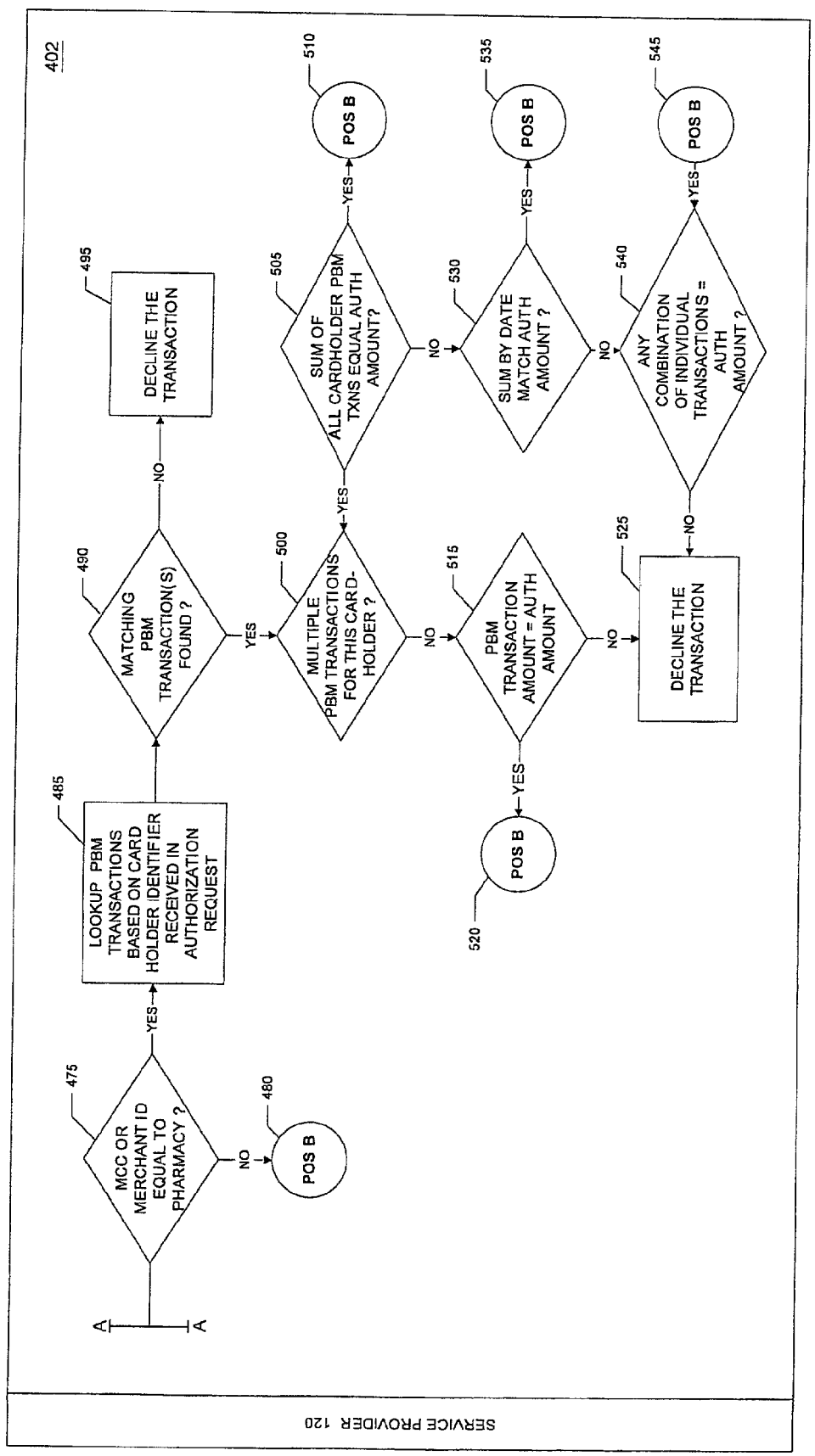
FIG. 4B depicts a second portion of a process for processing FSA transactions in accordance with the present invention.

Referring now to FIG. 4B, at step 475 the service provider 120 determines if the MCC or merchant identifier pertains to a pharmacy. If the MCC is on a list of potential merchant codes utilized by pharmacies 110, or if the merchant identifier is on a list of merchant identifiers designated by the service provider 120 as a pharmacy, the processing continues to step 485. If the MCC is not a pharmacy and the merchant identifier is not designated a pharmacy, the processing continues to step 480. At step 480, a message is transmitted to the pharmacy 110 rejecting the authorization request and the processing terminates. It will be appreciated that at any point if the processing terminates without authorization to the pharmacy 110, the employee 102 can submit a claim manually for reimbursement.

At step 485, the service provider 120 identifies the transaction and, thus, the employee 102 for which the authorization request was received by searching the payor transaction database 146. In the currently preferred embodiment of the present disclosure, the identification is based upon a match of the card holder identifier in the authorization request received in step 470 with the card holder identifier associated with the participant identifier as received in step 450.

At step 490, the service provider 120 determines if data relating to at least one transaction related to that employee 102 exists in the payor transaction database 146. Preferably, the data relating to the transaction(s) related to that employee 102 contains an amount identical to the PRB. As may be recognized by those skilled in the pertinent art based on the teachings herein, numerous fields or data items may be searched in order to find the data relating to the transaction(s) related to that employee 102. Each such method being in accordance with the present disclosure. If no data relating to the transaction(s) related to that employee 102 exists, the processing continues to step 495. At step 495, the service provider 120 transmits a message to the pharmacy 110 declining the authorization request and the employee 102 must pay the PRB by traditional methods.

If a matching transaction exists at step 490, the processing continues to step 500. At step 500, the service provider 120 determines if multiple transactions exist for the employee 102. If multiple transactions exist, the processing continues to step 505. At step 505, the service provider 120 sums the multiple transaction amounts received at step 450 and compares the sum with the amount of the PRB received via the authorization request at step 470. A verification occurs when the sum and the amount of the PRB are equal. If the sum is verified, the processing continues to step 510.

At step 510, the remaining transaction authorization steps occur. In a preferred embodiment, the remaining authorization steps include determining the status of the employee's 102 FSA card and an available FSA balance for the employee 102. If the FSA card status is active and the FSA has an adequate balance to pay the request, payment to the pharmacy is authorized, the respective FSA is correspondingly debited, and the balance of the respective FSA is updated; otherwise, the request is denied and the employee 102 pays by traditional methods If the sum is not verified, the processing continues to step 530.

If multiple matching transactions do not exist at step 500, the processing continues to step 515. At step 515, the service provider 120 verifies that the amount of the transaction received as part of the authorization request received at step 470 is equal to the amount of the transaction received at step 450. If the amounts match, the processing continues to step 520. At step 520, the remaining transaction authorization steps occur in the same manner as described above in connection with step 510. If the amounts do not match at step 515, the processing continues to step 525. At step 525, the authorization request is denied and the employee 102 may pay by traditional methods.

At step 530, the service provider determines if the amount of the transaction received in the authorization request in step 470 matches the sum of all transactions associated with the employee 102 for a particular date of service as received in step 450. If a match is located, the processing continues to step 535. At step 535, the remaining transaction authorization steps occur as noted above. If a date match is not located, the processing continues to step 540.

At step 540, the service provider 120 determines whether any combination of PRBs received at step 450 for the employee 102 is equal to the PRB of the authorization request received in step 470. As one example, an employee 102 may drop off a prescription on a Monday. The following day, the spouse of the employee 102 may drop off a prescription at the same pharmacy 110. On the subsequent Friday, the employee 102 may pick up both prescriptions. Thus, in this case, one authorization request will correspond to two records in the payor transaction database 146. Preferably, verification may be obtained by conducting a comparison against all combinations of amounts for the employee 102 in the payor transaction database 146 against the PRB. For example, Table 1 illustrates exemplary portions of several records within the payor transaction database 146 for an employee 102 having participant identifier "ABC123".

TABLE 1

| Participant Identifier | Dollar Amount |
|---|---|
| ABC123 | $10 |
| ABC123 | $15 |
| ABC123 | $25 |
| ABC123 | $20 |

Upon receipt of an authorization request having a fifty dollar PRB, for example, the service provider 120 would check each individual record against the incoming PRB and find no match. Similarly, the sum of all the transactions for employee 102 with participant identifier "ABC123" would not equal fifty dollars and verification would not occur. However, in accordance with a preferred embodiment of the present invention, the service provider 120 checks all possible combinations of the individual records for a suitable match. The result of each check yields either a result of "false" for no match or "true" for a match. A result of "true" allows for verification of the entire PRB. Table 2 illustrates an exemplary approach to analyzing the data of Table 1 for a fifty dollar PRB. Such an approach allows for substantiation of any combination of transactions within the pharmacy transaction database 146. If a proper combination exists, the processing continues to step 545.

TABLE 2

| Comparison | Match |
|---|---|
| 10 + 15 = 50? | False |
| 10 + 25 = 50? | False |
| 10 + 20 = 50? | False |
| 10 + 20 + 25 = 50? | False |
| 10 + 15 + 25 = 50? | True |

At step 545, the remaining transaction authorization steps occur as noted above. If no valid combination exists at step 540, the processing continues to step 525. At step 525, the authorization request is denied in a manner similar to step 495.

Preferably, the processor 140 of the server 122 provides access to the FSA for the employee 102 and employer 104. Accordingly, an advantage of the system and method of the present invention is that the service provider 120 may provide various FSA-related services, including, without limitation, presenting account history and balance information. Preferably, access is available through a secure Web site of the service provider 120. The employee 102 may access FSA information by using his or her personal computer 106 or via a LAN provided by the employer 104 or TPA 121.

In one embodiment, in return for providing the FSA cards and administering the FSAs, the service provider 120 receives a fee from the employer 104 or TPA 121. For example, the fee may consist of an annual license fee and a commission for each employee 102 who opens a FSA. Despite the costs, employers will be motivated to enroll with the service provider 120 because of the reduced administrative burden of processing FSA transactions and increased satisfaction among employees.

While the invention has been described with respect to preferred embodiments, those skilled in the art will readily appreciate that various changes and/or modifications can be made to the illustrated embodiment without departing from the spirit or scope of the invention as defined by the appended claims. For example, as indicated, the participating goods and/or service providers may include any of numerous different types of entities that are currently, or later become involved in the sale of goods or services involving reimbursable expenses under the IRS Code. Similarly, the payors may include PBMs and/or any of numerous other entities that are currently or later become known for performing the adjudication function, and thus enabling substantiation of allowable expenses in accordance with the present invention. Similarly, the eligibility database(s) may be maintained and updated in any of numerous different ways, and the manner in which the service provider searches the payor transaction database, and otherwise determines whether a matching transaction exists for purposes of substantiation, may be performed in any of numerous different ways that are currently known, or later become known for performing such functions described herein. Accordingly, this detailed description of preferred embodiments is to be taken in a illustrative, as opposed to a limiting sense.

What is claimed is:

1. A method for processing a request to authorize payment against an account for reimbursing patient responsible balances (PRBs), comprising the steps of:
   receiving from at least one payor data indicative of transactions involving adjudicated claims and associated PRBs;
   storing in a payor transaction database said data received from the at least one payor;
   receiving from a goods or service provider a request to authorize payment of a PRB against said account, wherein said account is associated with a customer in connection with a sales transaction between said customer and the goods or service provider; and
   initiating a substantiation process for the payment to the goods or service provider for the sales transaction prior to the authorization of the payment for the sales transaction, the substantiation process comprising:
   querying the payor transaction database;
   in the event that the payor transaction database contains transaction information of at least one transaction that matches said sales transaction, matching the transaction information to the sales transaction, then communicating to the goods or service provider authorization for payment of the PRB against the account, and settling the authorized payment of the PRB against the account; and
   in the event that the payor transaction database does not contain transaction information that matches said sales transaction, communicating to the goods or service provider a denial of payment of the payment of the PRB against the account.

2. A method as recited in claim 1, wherein the authorization request includes a card holder identifier and a requested amount.

3. A method as recited in claim 2, wherein the authorization request further includes a me chant identifier, a merchant category code, and date and time of the transaction.

4. A method as recited in claim 2, further comprising the step of associating the data received from the at least one payor with at least one card holder identifier, and querying the payor transaction database based on the card holder identifier.

5. A method as recited in claim 1, further comprising the steps of storing data received from a health care administrator in an eligibility database, and verifying eligibility for the customer based upon querying the eligibility database.

6. A method as recited in claim 5, further comprising the step of updating the eligibility database on a periodic basis.

7. A method as recited in claim 4, further comprising the step of mapping at least one participant identifier to a plurality of card holder identifiers.

8. A method as recited in claim 1, wherein the goods or service provider is a pharmacy, and the payor is a pharmacy benefit manager (PBM).

9. A method as recited in claim 1, wherein the matching of the sales transaction to the at least one transaction in the payor transaction database is based on the amount of the PRB in the authorization request.

10. A method as recited in claim 1, wherein the step of querying the payor transaction database further includes the step of determining whether multiple transactions that are associated with a respective customer exist in the payor transaction database.

11. A method as recited in claim 9, wherein the step of querying the payor transaction database further includes the step of summing the PRBs of multiple transactions associated with a respective customer in the payor transaction database to yield a summed amount and comparing the summed amount to the PRB of the authorization request.

12. A method as recited in claim 9, wherein the step of querying the payor transaction database further includes the step of comparing the PRB of the authorization request against a plurality of different combinations of PRBs associated with a respective customer in the payor transaction database.

13. A method as recited in claim 9, wherein the step of querying the payor transaction database further includes the step of comparing the PRB of the authorization request against the sum of all PRBs associated with a respective customer on a respective data.

14. A system for processing a request to authorize payment against an account for reimbursing patient responsible balances (PRBs), comprising:
    first means for storing in a payor transaction database data received from at least one payor indicative of transactions involving adjudicated claims and associated PRBs;
    second means for receiving from a goods or service provider a request to authorize payment of a PRB against said account, wherein said account is associated with a customer in connection with a sales transaction between said customer and the goods or service provider;
    third means for initiating a substantiation process for the payment to the goods or service provider for the sales transaction prior to the authorization of the payment for the sales transaction and querying the payor transaction database for at least one transaction that matches said sales transaction;
    fourth means for matching the at least one transaction to the sales transaction, authorizing payment of the PRB against the account, and settling the authorized payment of the PRB against the account;
    fifth means for then communicating to the goods or service provider authorization for the payment of the PRB against the account and if the payor transaction database does not contain the at least one transaction that matches said sales transaction, communicating to the goods or service provider a denial of the payment of the PRB against the account.

15. A system as recited in claim 14, wherein the first means includes a computer memory.

16. A system as recited in claim 14, wherein the second means includes a modem.

17. A system as recited in claim 14, wherein the third means includes a processor.

18. A system as recited in claim 14, wherein the fourth means includes a processor.

19. A system as recited in claim 14, wherein the fifth means includes a modem.

20. A system as recited in claim 14, further comprising at least one housing for containing and operatively connecting the first, second, third, fourth, and fifth means.

21. A system as recited in claim 14, wherein the goods or service provider is a pharmacy, and the payor is a pharmacy benefit manager (PBM).

22. A system as recited in claim 14, wherein the authorization request of the second means includes at least a card holder identifier and a requested PRB amount.

23. A system as recited in claim 22, further comprising means for associating the data received from the at least one payor with at least one card holder identifier, and wherein the third means is queries the payor transaction database based on the at least one card holder identifier.

24. A system as recited in claim 14, wherein the matching of the sales transaction to the transaction in the payor transaction database is based on the amount of the PRB in the request.

25. A system as recited in claim 14, wherein the third means determines whether multiple transactions that are associated with the respective customer exist in the payor transaction database.

26. A system as recited in claim 25, further comprising means for summing the PRBs of multiple transactions associated with a respective customer in the payor transaction database to yield a summed amount, and comparing the summed amount to the PRB of the authorization request.

27. A system as recited in claim 25, further comprising means for comparing the PRB of tie authorization request against a plurality of different combinations of PRBs associated with a respective customer in the payor transaction database.

28. A system as recited in claim 25, further comprising means for comparing the PRB of tile authorization request against a sum of all PRBs associated with a respective customer on a respective date in the payor transaction database.

29. A system for processing a request to authorize payment against an account for reimbursing patient responsible balances (PRBs), comprising:
    at least one memory configured for storing a program and a payor transaction database of transactions it involving adjudicated claims and associated PRBs; and
    at least one processor in communication with the at least one memory, wherein the at least one processor is configured for:
    receiving from a goods or service provider a request to authorize payment of a PRB against said account, wherein said account is associated with a customer in connection with a sales transaction between said customer and the goods or service provider; and initiating a substantiation process for the payment to the goods or service provider for the sales transaction prior to the authorization of the payment for the sales transaction, the substantiation process comprising:

querying the payor transaction database;

in the event that the payor transaction database contains transaction information of at least one transaction that matches said sales transaction, matching the transaction information to the sales transaction, then communicating to the goods or services provider authorization for payment of the PRB against the account, settling the authorized payment of the PRB against the account; and in the event that the payor transaction database does not contain transaction information that matches said sales transaction, communicating to the goods or service provider a denial of payment of the payment of the PRB against the account.

30. A system as recited in claim 29, wherein the matching of the sales transaction to the transaction in the payor transaction database is based on the amount of the PRB in the request.

31. A system as recited in claim 29, wherein the at least one processor is further configured to determine whether multiple transactions that are associated with the respective customer exist in the payor transaction database.

32. A system as recited in claim 31, wherein the at least one processor is further configured to determine whether there is at least one transaction in the payor transaction database that matches the sales transaction of the authorization request by summing the PRBs of multiple transactions associated with a respective customer in the payor transaction database to yield a summed amount, and comparing the summed amount to the PRB of the authorization request.

33. A system as recited in claim 31, wherein the at least one processor is further configured to determine whether there is at least one transaction in the payor transaction database that matches the sales transaction of the authorization request by comparing the PRB of the authorization request against a plurality of different combinations of PRBs associated with a respective customer in the payor transaction database.

34. A system as recited in claim 31, wherein the at least one processor is further configured to determine whether there is at least one transaction in the payor transaction database that matches the sales transaction of the authorization request by comparing the PRB of the authorization request against a sum of all PRBs associated with a respective customer on a respective data.

35. A method as recited in claim 1, further comprising the step of determining whether to authorize payment of the PRB against the respective account based upon the query of the payor transaction database.

36. A method as recited in claim 1, further comprising the step of corresponding debiting the respective account in the amount of the PRB, if the query of the payor transaction database reveals at least one transaction that matches said sales transaction, occurs prior to the step of communicating to the goods or service provider either authorization of payment of the PRB against the respective account or denial of the request to authorize payment.

37. A method as recited in claim 1, wherein the account is a pre-tax account.

38. A method as recited in claim 37, wherein the pre-tax account is a flexible spending account (FSA).

39. A system as recited in claim 14, further comprising means for determining whether to authorize payment of the PRB against the respective account based Upon the query of the payor transaction database.

40. A system as recited in claim 14, wherein the account is a pre-tax account.

41. A system as recited in claim 40, wherein the pre-tax account is a flexible spending account (FSA).

42. A system as recited in claim 29, wherein the at least one processor is configured for determining whether to authorize payment of the PRB against the account based upon the query of the payor transaction database.

43. A system as recited in claim 29, wherein the at least one processor is configured for debiting the respective account in the amount of the PRB, if the query of the payor transaction database reveals at least one transaction that matches said sales transaction, prior to communicating to the goods or service provider either authorization of payment of the PRB against the respective account or denial of the request to authorize payment.

44. A system as recited in claim 29, wherein the account is a pre-tax account.

45. A system as recited in claim 44, wherein the pre-tax account is a flexible spending account (FSA).

46. A method as recited in claim 29, wherein the goods or service provider is a pharmacy.

* * * * *

UNITED STATES PATENT AND TRADEMARK OFFICE
CERTIFICATE OF CORRECTION

| | | |
|---|---|---|
| PATENT NO. | : 7,174,302 B2 | |
| APPLICATION NO. | : 09/878891 | |
| DATED | : February 6, 2007 | |
| INVENTOR(S) | : Robert E. Patricelli, Christopher M. Byrd and Paul L. Chabot | |

It is certified that error appears in the above-identified patent and that said Letters Patent is hereby corrected as shown below:

On the Title Page, Item (73), the city of the assignee should read --Avon--.

Column 14, line 65, "me chant" should read --merchant--.

Column 15, line 44, "data" should read --date--.

Column 16, line 31, "is" should be deleted.

Column 16, line 47, "tie" should read --the--.

Column 16, line 52, "tile" should read --the--.

Column 16, line 60, "it" should be deleted.

Column 18, line 4, "data" should read -- date--.

Column 18, line 10, "corresponding" should read --correspondingly--.

Signed and Sealed this

Twenty-ninth Day of May, 2007

JON W. DUDAS
*Director of the United States Patent and Trademark Office*